US007908151B2

(12) United States Patent
Heckerman et al.

(10) Patent No.: US 7,908,151 B2
(45) Date of Patent: Mar. 15, 2011

(54) GET PREP QUESTIONS TO ASK DOCTOR

(75) Inventors: David E. Heckerman, Bellevue, WA (US); Pablo Argon, Redmond, WA (US); Behrooz Chitsaz, Bellevue, WA (US); Hong L. Choing, Collegeville, PA (US); James R. Hamilton, Bellevue, WA (US); Nuria M. Oliver, Seattle, WA (US); Vladimir G. Sadovsky, Redmond, WA (US); Chris Demetrios Karkanias, Sammamish, WA (US); Hurbert Van Hoof, Seattle, WA (US); Oren Rosenbloom, Redmond, WA (US)

(73) Assignee: Microsoft Corporation, Redmond, WA (US)

( * ) Notice: Subject to any disclaimer, the term of this patent is extended or adjusted under 35 U.S.C. 154(b) by 767 days.

(21) Appl. No.: 11/864,599

(22) Filed: Sep. 28, 2007

(65) Prior Publication Data
US 2009/0089082 A1 Apr. 2, 2009

(51) Int. Cl.
G06Q 10/00 (2006.01)
G06Q 50/00 (2006.01)
(52) U.S. Cl. .................................... 705/2; 705/3
(58) Field of Classification Search ................ 705/2, 3, 705/10; 600/300
See application file for complete search history.

(56) References Cited

U.S. PATENT DOCUMENTS

| 5,517,405 | A | 5/1996 | McAndrew et al. |
|---|---|---|---|
| 5,572,421 | A | 11/1996 | Altman et al. |
| 6,047,259 | A | 4/2000 | Campbell et al. |
| 6,108,665 | A | 8/2000 | Bair et al. |
| 6,607,482 | B1 | 8/2003 | Teitelbaum |
| 7,056,289 | B2 | 6/2006 | Kasper et al. |
| 7,213,009 | B2 | 5/2007 | Pestotnik et al. |
| 7,260,480 | B1 | 8/2007 | Brown et al. |
| 2002/0029157 | A1 | 3/2002 | Marchosky |
| 2007/0213604 | A1 | 9/2007 | Brown |
| 2009/0125322 | A9* | 5/2009 | Dahlin et al. ............... 705/2 |

OTHER PUBLICATIONS

The Analyst http://www.diagnose-me.com/?page=dian&gclid=CMnTz_r8qY8CFQwdEgodpDwLRw. Last accessed Oct. 26, 2007, 3 pages.

* cited by examiner

Primary Examiner — Luke Gilligan
(74) Attorney, Agent, or Firm — Lee & Hayes, PLLC

(57) ABSTRACT

The claimed subject matter provides a system and/or a method that facilitates dynamically providing a question to ask a medical professional during an appointment. An interface can receive a portion of medical data. A counselor component can generate a question based on the portion of medical data, wherein the question is generated to elicit an answer from a medical professional during an appointment. Moreover, the counselor component can dynamically generate a second question directed toward the medical professional based upon at least one of the answer or a value of information (VOI) computation.

20 Claims, 12 Drawing Sheets

GET PREP QUESTIONS TO ASK DOCTOR

BACKGROUND

Technological advances in computer hardware, software and networking have lead to increased demand for electronic information exchange rather than through conventional techniques such as paper and telephone correspondence, for example. Such electronic communication can provide split-second, reliable data transfer between essentially any two locations throughout the world. Many industries and consumers are leveraging such technology to improve efficiency and decrease cost through web-based (e.g., on-line) services. For example, consumers can purchase goods, review bank statements, research products and companies, obtain real-time stock quotes, download brochures, etc. with the click of a mouse and at the convenience of home.

As the amount of available electronic data grows, it becomes more important to store and/or utilize such data in a manageable manner that facilitates user-friendly and quick data searches and retrieval and data mining. In particular, the Healthcare industry has aggressively migrated toward electronic storage of the medical record and electronic information exchange in terms of health-related data, doctor profiles, hospital reviews, etc. For example, numerous web sites and forums offer a wealth of information in connection with general medical information (e.g., definitions, overviews, terminology, treatments, side-affects, etc.), diagnosis (e.g., symptoms, prescriptions, treatment, etc.), and medical physicians or facilities (e.g., hospital reviews, physician biographies, etc.).

Yet, various problems surface in obtaining healthcare information via the web since there is an overwhelming amount of available information. In general, the format and file types associated with medical data is almost as plentiful as the amount of data available on the web. In other words, compatibility and usability for medical data becomes extremely difficult in light of the file types, formats, etc. that may be specific to applications, software, hardware, devices, and the like. As stated, there is a large amount of medical data available to the public. For example, a search engine query with the terms "flu symptoms" can return millions of results. Sorting, let alone, finding relevant data within these results can turn into quite the hassle (even though the search may have yielded an answer for the query). Generally, accessing medical or healthcare data can be fairly simple with a search engine but identifying user relevant information can be extremely time-consuming. Moreover, there are various problems associated with mining this medical or healthcare data including the medical record, as there is no common schema for the data.

Regardless of the amount of healthcare knowledge a patient may have, the patient typically asks a medical professional questions during a check-up, an appointment, or urgent care appointment. For instance, during a general check-up, a patient may ask general questions related toward exercise, eating, lifestyle, etc. In another example, a specific appointment for a disease or symptom may result in a patient asking a question about treatment, side-affects, prescriptions, etc. Yet, most patients either forget to ask questions or come up with additional questions after leaving an appointment. Moreover, medical professionals tend to answer as many questions as a patient can offer during an appointment yet answering questions outside these scheduled appointments can be time consuming and costly (e.g., time, money, availability for other patients, etc.). For example, medical professionals typically cannot afford to spend time answering questions on the Internet, over the phone, or entering information onto computers.

Still further, the United States spends 60% more per person on health care than any other nation, yet in overall quality of its care ranks $37^{th}$ in the world. Also, 40% of Americans with health problems do not get treatment or medication due to cost. In Pay-for-Quality (P4Q) programs from Health Plans and other Sponsors; the goal is to put Providers in control of improving care quality and coordination, while giving Payers access to the point-of-care (e.g., communication, coordination and key clinical data, etc.) for improving the effectiveness of their Disease Management, Case Management and Consumer Self-Management programs. No major solutions have emerged yet to tackle such big problems to date.

SUMMARY

The following presents a simplified summary of the innovation in order to provide a basic understanding of some aspects described herein. This summary is not an extensive overview of the claimed subject matter. It is intended to neither identify key or critical elements of the claimed subject matter nor delineate the scope of the subject innovation. Its sole purpose is to present some concepts of the claimed subject matter in a simplified form as a prelude to the more detailed description that is presented later.

The subject innovation relates to systems and/or methods that facilitate generating a question to ask a medical professional during a medical examination. A patient can be assisted with the automated or semi automated system, comprised of a combination of computerized hardware and/or software with interactive components. One of the interactive components can be a counselor component that directly generates user assistance in a form of user communicated counseling. The counselor component can automatically generate a question to elicit an answer from a medical professional based upon a portion of medical data. The counselor component can be utilized with a portable device in which a patient can be communicated a question that is to be asked to a medical professional. By automatically supplying the patient with medical questions via a portable device, an appointment between the medical professional and the patient is greatly enhanced since the patient can ask any possible questions he or she may have and the medical professional answers all of the patients questions. The counselor component can utilize various techniques in order to identify relevant and/or most suitable questions such as a value of information (VOI) computation algorithm or a predetermined decision tree.

In accordance with one aspect of the subject innovation, the counselor component can employ an aggregator component that can capture a statement, an answer, or a response from the medical professional in a standardized, uniform manner. Thus, a universal and uniform schema can be utilized to collect the responses, answers, and statements in connection with an appointment with the medical professional. In yet another aspect, the counselor component can employ a reminder component that can communicate a reminder to a patient or a medical professional in connection with an appointment between the two.

In still another aspect of the subject innovation, the counselor component can generate an additional question in light of an answer or response to an automatically generated question, wherein the additional question can be directed to the medical professional. Moreover, the counselor component can utilize a log component that can record a user-defined question to pose to the medical professional. Additionally, the log component can record any responses, answers, or statements from the medical professional. In other aspects of the claimed subject matter, methods are provided that facilitate identifying a series of questions for a medical professional that can be displayed on device during an appointment.

The following description and the annexed drawings set forth in detail certain illustrative aspects of the claimed subject matter. These aspects are indicative, however, of but a few of the various ways in which the principles of the innovation may be employed and the claimed subject matter is intended to include all such aspects and their equivalents. Other advantages and novel features of the claimed subject matter will become apparent from the following detailed description of the innovation when considered in conjunction with the drawings.

DETAILED DESCRIPTION

Figure 1:
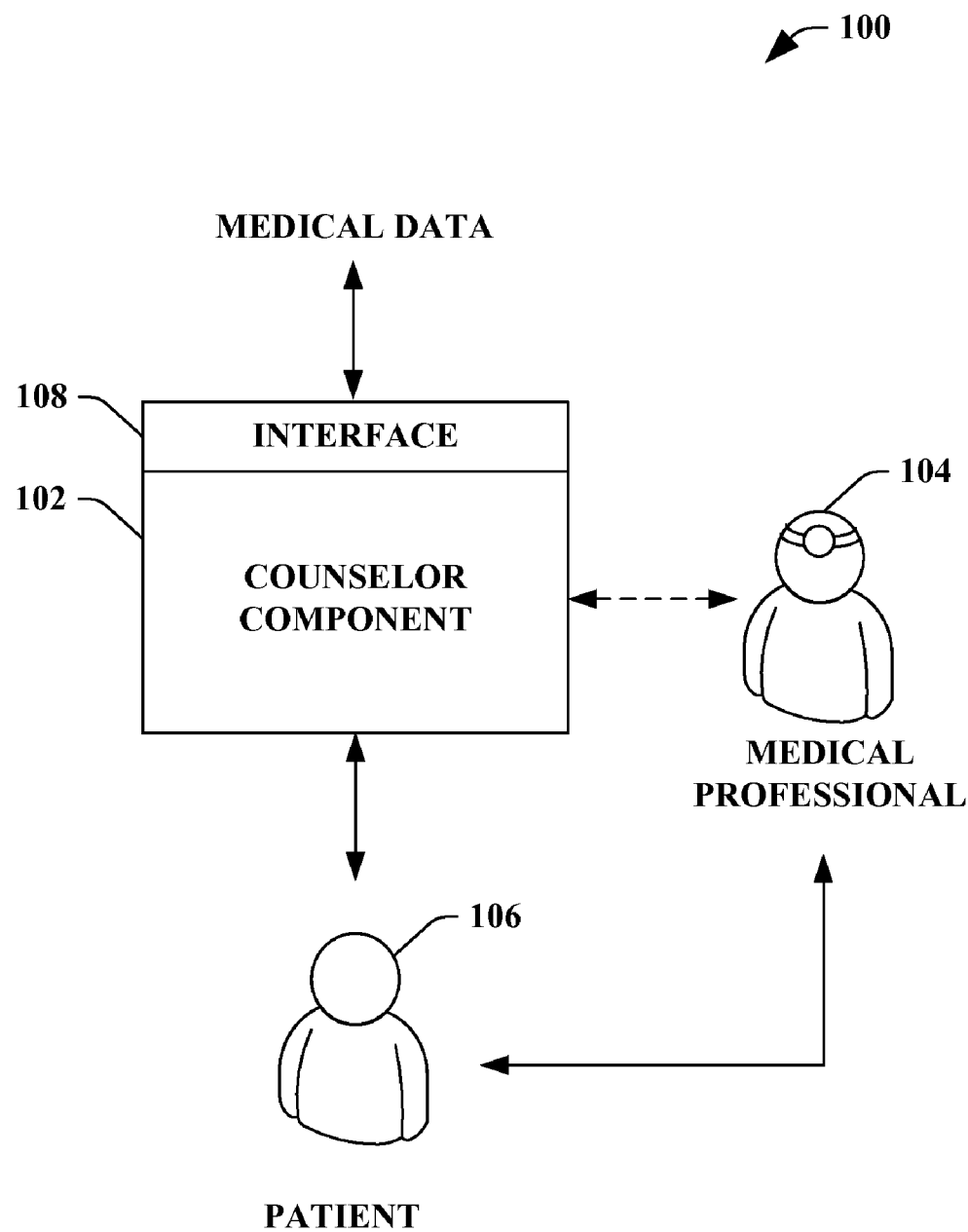
FIG. 1 illustrates a block diagram of an exemplary system that facilitates generating a question to ask a medical professional during a medical examination.

The claimed subject matter is described with reference to the drawings, wherein like reference numerals are used to refer to like elements throughout. In the following description, for purposes of explanation, numerous specific details are set forth in order to provide a thorough understanding of the subject innovation. It may be evident, however, that the claimed subject matter may be practiced without these specific details. In other instances, well-known structures and devices are shown in block diagram form in order to facilitate describing the subject innovation.

As utilized herein, terms "component," "system," "interface," "store," "device," "network," "cloud," and the like are intended to refer to a computer-related entity, either hardware, software (e.g., in execution), and/or firmware. For example, a component can be a process running on a processor, a processor, an object, an executable, a program, a function, a library, a subroutine, and/or a computer or a combination of software and hardware. By way of illustration, both an application running on a server and the server can be a component. One or more components can reside within a process and a component can be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick, key drive . . . ). Additionally it should be appreciated that a carrier wave can be employed to carry computer-readable electronic data such as those used in transmitting and receiving electronic mail or in accessing a network such as the Internet or a local area network (LAN). Specifically, the subject innovation can be utilized with a variety of hardware configurations such as, but not limited to disability assisted input/output facilities, voice enabled input/output, dactyl (e.g., Braille, etc.) keyboard, etc. Of course, those skilled in the art will recognize many modifications may be made to this configuration without departing from the scope or spirit of the claimed subject matter. Moreover, the word "exemplary" is used herein to mean serving as an example, instance, or illustration. Any aspect or design described herein as "exemplary" is not necessarily to be construed as preferred or advantageous over other aspects or designs.

Now turning to the figures, FIG. 1 illustrates a system 100 that facilitates generating a question to ask a medical professional during a medical examination. The system 100 can include a counselor component 102 that can receive a portion of medical data via an interface component 108 (discussed in more detail below) and automatically generate a question that is to elicit an answer from a medical professional 104. In particular, the counselor component 102 can dynamically generate a question for a patient 106 to ask the medical professional 104 during an appointment based at least in part upon evaluation of a portion of medical data. The counselor component 102 can further generate additional questions based upon an answer from the medical professional 104, wherein the answer can be in response to a question previously automatically generated. It is to be appreciated that the medical professional can be any suitable medical related entity such as, but not limited to, a doctor, a nurse, a specialist, a surgeon, a medical student, a resident, a medical assistant, etc.

For example, most patients do not ask efficient questions or all the questions they would like during an appointment with a medical professional. The subject innovation solves such problems by automatically providing questions to a patient in order for the patient to pose towards a medical professional during an appointment. Thus, in one instance, a patient can have an appointment with a doctor for his or her back pain. Medical data related to the patient and/or the diagnosis (in this example the diagnosis is back pain) can be evaluated in order to generate a question to elicit an answer from the doctor. The question can be, for example, "what treatment do you recommend?" This question can be directed to the doctor and the patient can await an answer. Once the answer is received, an additional question can be generated based on a received response. By automatically identifying questions, the appointment with the doctor and patient is optimized and more efficient. Moreover, the doctor and the patient both benefit since the doctor is answering all of the patients questions in a timely manner and the patient is getting all the information they desire.

In one specific example, the patient 106 interacts with the medical professional 104 in order to ask automatically generated questions and receive answers. The patient 106 can interact with the counselor component 102 to alleviate direct communication with the medical professional. Thus, the patient 106 can be provided the questions from the counselor component 102 whereas the answers from the medical professional 104 can be communicated by the patient 106 to the counselor component. However, in another example, the questions can be communicated to the patient 106 and the answers can be received by the counselor component 102 directly from the medical professional 104. For instance, the counselor component 102 can utilize speech recognition on a verbal answer from the medical professional 104 to allow additional questions to be generated from such response.

In accordance with an aspect of the subject innovation, the counselor component 102 can employ value of information (VOI) computations to facilitate identifying or generating questions. Specifically, the counselor component 102 can utilize technical algorithms associated with determining the value of information, wherein such algorithms can identify a question to ask a doctor. For instance, the counselor component 102 can generate any suitable number of questions based on medical data and/or an answer received from the medical professional 104. By utilizing value of information computations, the questions can be organized in a hierarchical manner based on importance for each specific appointment or situation. VOI algorithms pinpoint questions that provide the most information or, more generally, the most value to the patient, given the current state of information about that patient. In general, the counselor component 102 can generate a question by utilizing a dictionary, a branching logic (e.g., decision tree) algorithm, or machine-learning algorithms that use VOI computations to identify those questions whose answers are most informative in an information-theoretic or decision-analytic sense.

The counselor component 102 can evaluate medical data in order to provide at least one question directed toward the medical professional 104. For example, the medical data can be any suitable data related to healthcare such as, but not limited to, a diagnosis, a prognosis, a medical record, a symptom, a medical evaluation, a prior medical condition, a medical condition, a disease, a virus, a blood type, an allergy, a test result, a blood pressure reading, a heart rate, an x-ray, an MRI, a scan, a CAT scan, a blood work result, a medical chart, a reading from a medical device, or a portion of information from a medical facility. Moreover, it is to be appreciated and understood that the counselor component 102 can automatically generate a question based on the medical data prior to an appointment, dynamically during an appointment, and/or any suitable combination thereof. In an additional example, the counselor component 102 can enable the patient 106 to sort (e.g., filter, delete, re-arrange order of questions, etc.) the automatically generated questions for an appointment (discussed in more detail in FIG. 7).

It is to be appreciated that by allowing the patient to enter the data, the doctor or medical professional has a method/system for plausible deniability by employing the subject innovation. In other words, the medical professional can not be easily sued in a court of law (e.g., malpractice suits, etc.). In addition, most medical professionals feel compelled to answer patient questions while in the presence of such medical professionals. However, medical professionals are difficult to reach after a visit, appointment, etc. The system 100 can ensure that patients get their questions answered while they can (e.g., during the presence of the medical professional). Moreover, because you have a patient (who wants lots of information) asking questions of a medical professional in their presence, there is an opportunity to import more data into a medical record than otherwise.

In addition, the system 100 can include any suitable and/or necessary interface component 108 (herein referred to as "interface 108"), which provides various adapters, connectors, channels, communication paths, etc. to integrate the counselor component 102 into virtually any operating and/or database system(s) and/or with one another. In addition, the interface 108 can provide various adapters, connectors, channels, communication paths, etc., that provide for interaction with the counselor component 102, the medical professional 104, the patient 106, medical data, and any other device and/or component associated with the system 100.

Figure 2:
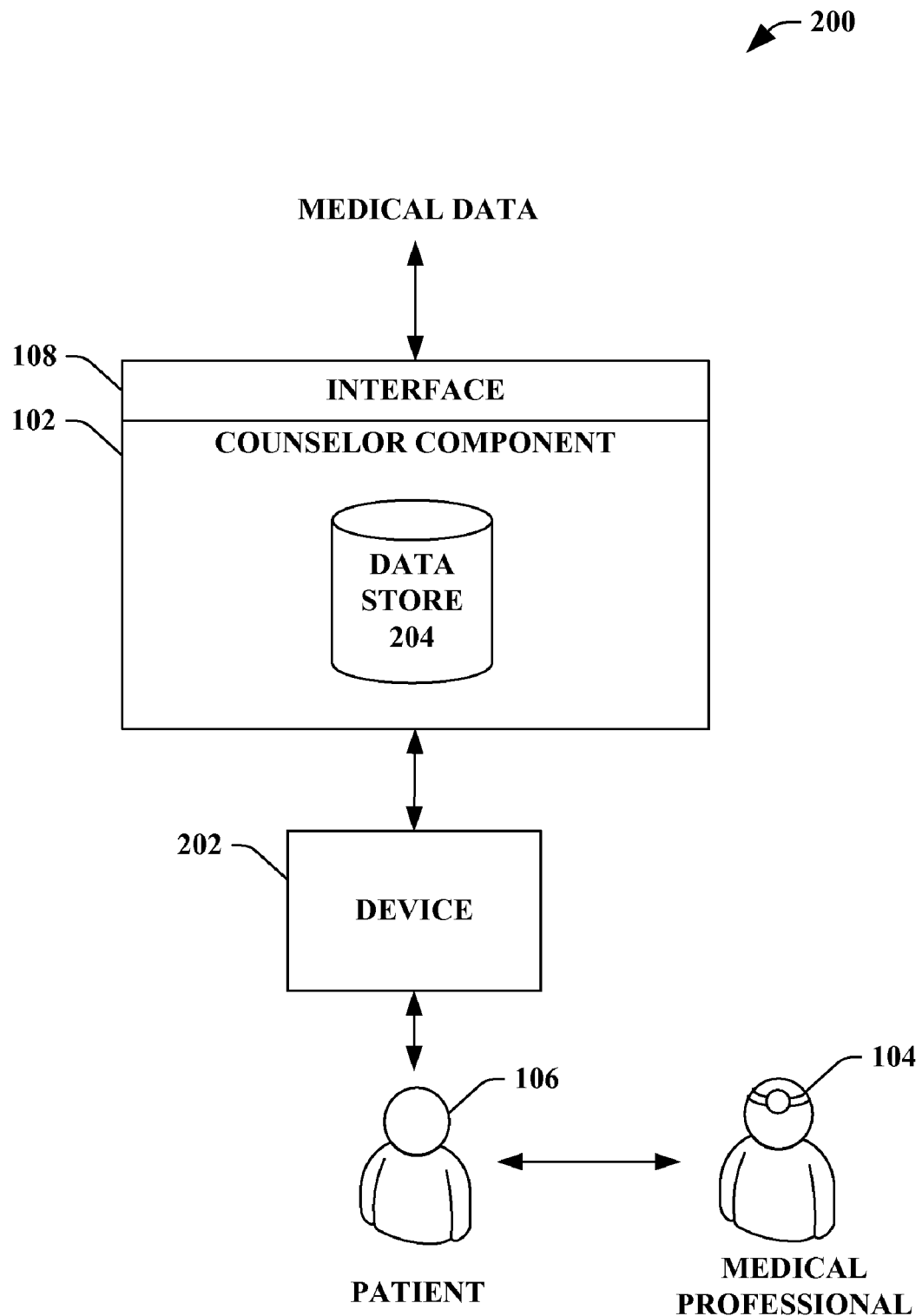
FIG. 2 illustrates a block diagram of an exemplary system that facilitates identifying a series of questions for a medical professional that can be displayed on device during an appointment.

FIG. 2 illustrates a system 200 that facilitates identifying a series of questions for a medical professional that can be displayed on device during an appointment. The system 200 can include the counselor component 102 that can automatically produce a question that elicits an answer or response from the medical professional 104. The counselor component 102 can be utilized with a device 202, wherein the device 202 can display and/or inform the generated question to the patient 106. It is to be appreciated that the counselor component 102 can be utilized with the device 202, be incorporated into the device 202, and/or any suitable combination thereof.

The device 202 can be any suitable device that can receive a question and communicate such question. For instance, the device 202 can be a smartphone, a portable device, a cell phone, a mobile communication device, a portable digital assistant (PDA), a laptop, a pocket PC, a desktop, a gaming device, a portable media player, a media device, a tablet PC, a handheld, a wireless browsing device, an electronic organizer, a gaming console, a device with Internet connectivity, etc. In one example, the counselor component 102 can dynamically create a question which can be displayed or communicated to the patient 106. The patient 106 can ask the question to the medical professional 104 in order to receive a response, a statement, and/or an answer. In one aspect, the patient 106 can input the answer or response from the medical professional 104 into the device 202 to allow the counselor component 102 to generate an additional question. In another aspect, the device 202 and/or the counselor component 102 can automatically receive the answer or response from the medical professional 104. For instance, the device 202 and/or the counselor component 102 can utilize voice recognition to comprehend and track the response or answer given by the medical professional 104.

The system 200 can further include a data store 204 that can include any suitable data related to the counselor component 102, the device 202, the patient 106, the medical professional 104, etc. For example, the data store 204 can include, but not limited to including, medical data, general medical data, medical records for a patient, medical professional information (e.g., specialty, education, biography, etc.), questions, VOI computations, patient data (e.g., diagnosis, history, medical data, etc.), answers from the medical professional, responses from the medical professional, voice recognition techniques, configurations, user profiles, settings, options, and/or any other suitable data related to the system 200.

It is to be appreciated that the data store 204 can be, for example, either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable programmable ROM (EEPROM), or flash memory. Volatile memory can include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), Rambus direct RAM (RDRAM), direct Rambus dynamic RAM (DRDRAM), and Rambus dynamic RAM (RDRAM). The data store 204 of the subject systems and methods is intended to comprise, without being limited to, these and any other suitable types of memory. In addition, it is to be appreciated that the data store 204 can be a server, a database, a hard drive, a pen drive, an external hard drive, a portable hard drive, and the like. Moreover, the system 200 can utilize multiple data stores that can be employed by the counselor component 102, wherein the data stores can be aggregated throughout multiple physical components, for instance, built in hard drive coupled with removable flash card (e.g., personalized and uniquely identifies to a given patient 106).

Figure 3:
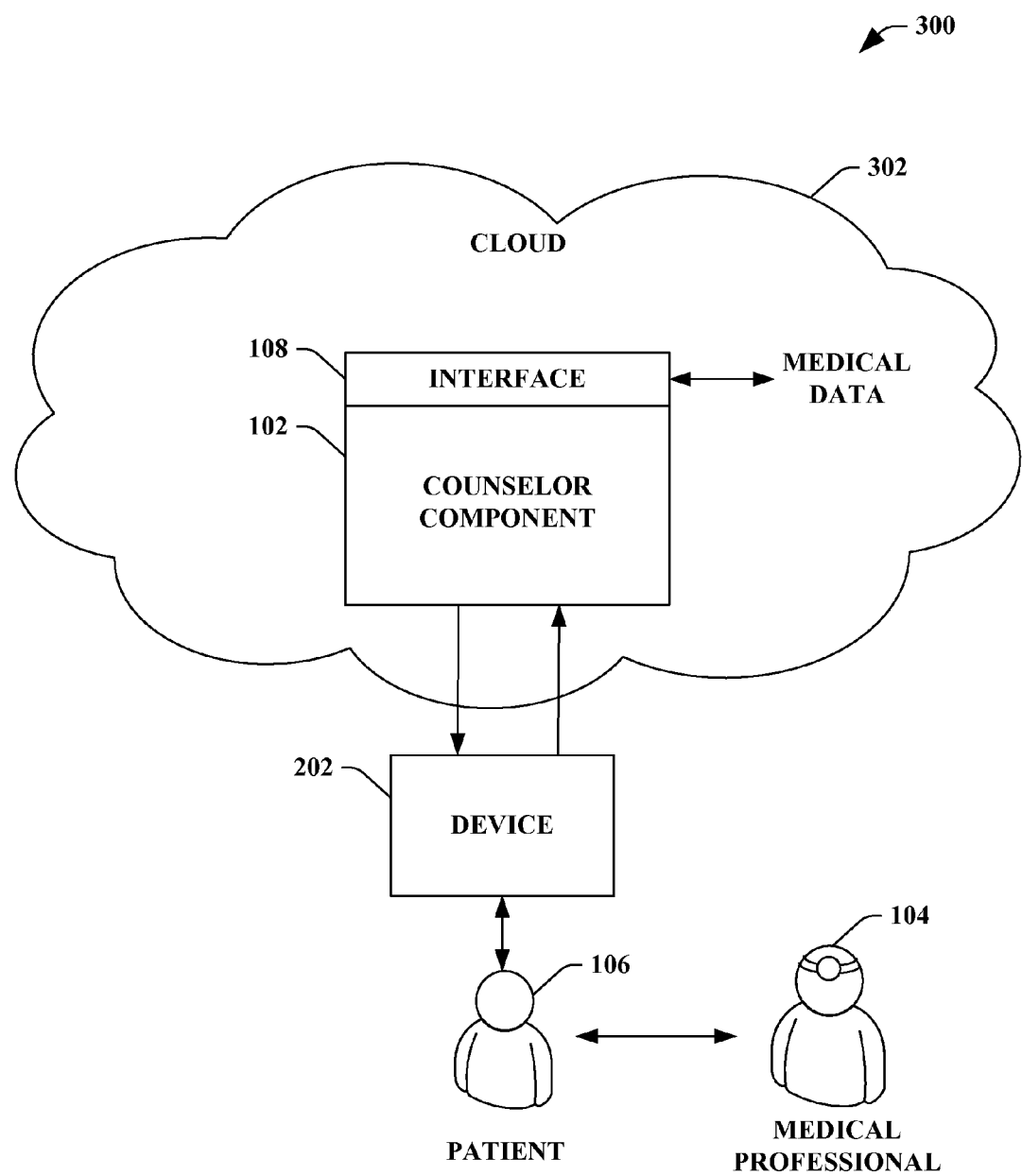
FIG. 3 illustrates a block diagram of an exemplary system that facilitates generating a question for a medical professional in accordance with an aspect of the subject innovation.

FIG. 3 illustrates a system 300 that facilitates generating a question for a medical professional in accordance with an aspect of the subject innovation. The system 300 can include the counselor component 102 that can seamlessly and dynamically generate a question to elicit an answer or response from the medical professional 104, wherein the question is based upon at least one of medical data, general medical knowledge, a medical history for the patient 106, a prognosis, a diagnosis, an answer from the medical professional 104, a statement from the medical professional 104, and/or a response from the medical professional 104. Moreover, the counselor component 102 can interact with the device 202 in order to provide questions, receive answers, etc. in connection with a medical appointment.

The system 300 is depicted with the counselor component 102 incorporated within a cloud 302. The cloud 302 can refer to any collection of resources (e.g., hardware, software, combination thereof, etc.) that are maintained by a party (e.g., off-site, on-site, third party, etc.) and accessible by an identified user over a network (e.g., Internet, wireless, LAN, cellular, Wi-Fi, WAN, etc.). The cloud 302 is intended to include any service, network service, cloud service, collection of resources, etc. and can be accessed by an identified user via a network. In addition, the cloud 302 can provide any suitable number of service(s) to any suitable number of user(s) and/or client(s). In particular, the cloud 302 can include resources and/or services that generate a question directed to the medical professional 104. For instance, the counselor component 102 can be incorporated into the cloud 302 which can push and/or pull information (e.g., questions, answers, etc.) to the device 202. Furthermore, the system 300 can be a distributed configuration or a rich client. In such distributed configuration or rich client, the device 202 can include a portion of the counselor component 102 immediately interacting with the user, while the cloud 302 hosts another portion.

Central to any information intensive profession is the ability to collect, store, validate, analyze, and share information in ways that decisions and actions can be made possible. Doctors or care providers can use this information to proactively provide better patient care. An application or software can do the required analysis of the available patient data in the cloud 302 prior to the arrival of the patient such that certain health conditions, prescriptions, appointments, lab results are consider to ensure all required questions are prominently displayed to ask the patient or medical professional during an appointment. Such information could also be used to remind patient to take their medicines, go get lab work, and show up for schedule doctor visits. This would translate into a huge cost saver for Payors (Health Plans and Employers) and Providers. Getting prep questions to ask doctors (patient perspective) and having informed prep questions to ask patient (doctor's perspective) compliments each other toward better patient care.

Figure 4:
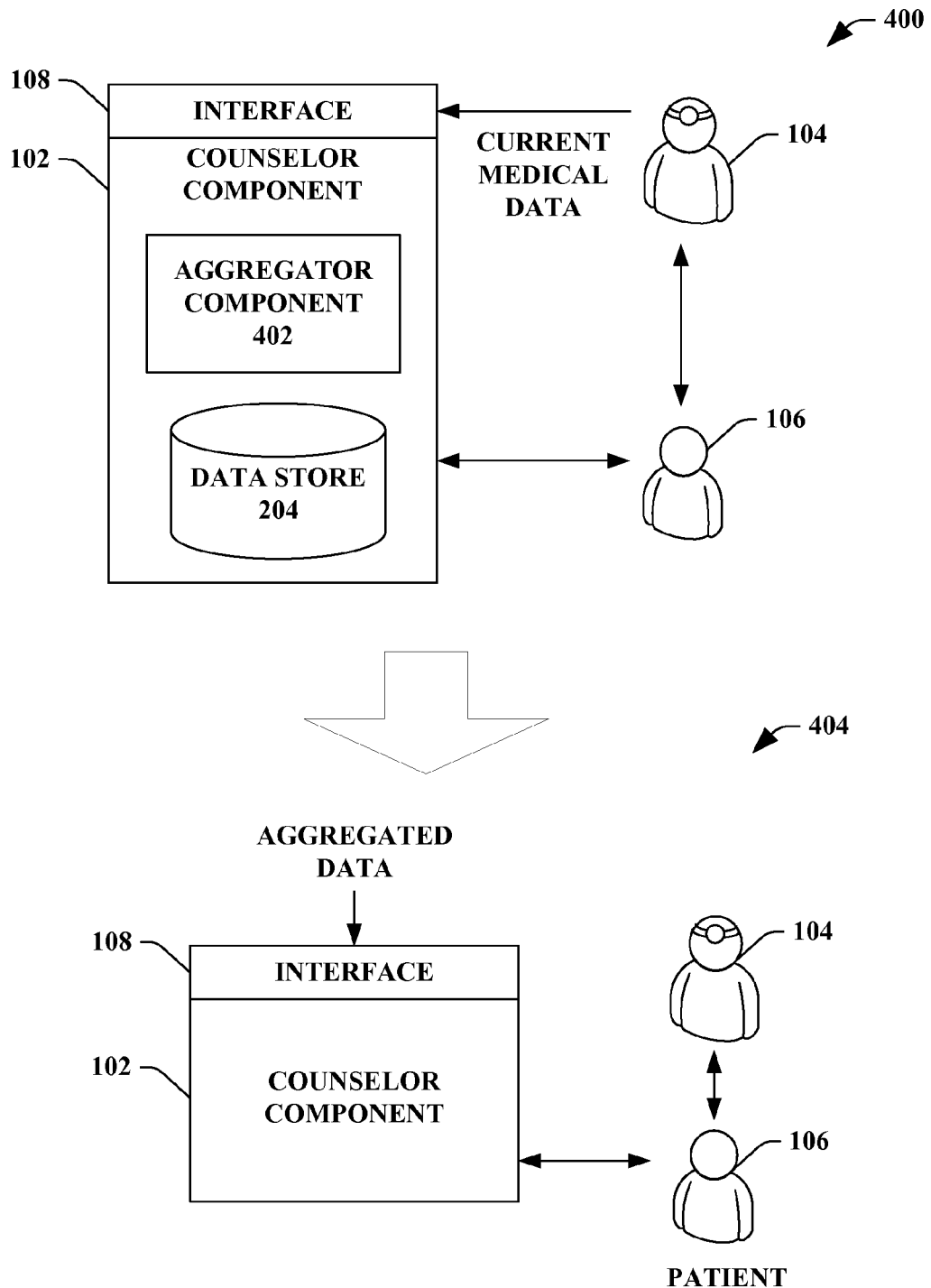
FIG. 4 illustrates a block diagram of an exemplary system that facilitates uniformly collecting a plurality of answers from medical professionals in which to leverage for question generation.

FIG. 4 illustrates a system 400 that facilitates uniformly collecting a plurality of answers from medical professionals in which to leverage for question generation. FIG. 4 illustrates a system 400 that collects an answer, a statement, and/or a response from the medical professional 104 in order to create a "clean" source of information that can be organized in a standardized format. The system 400 can include the counselor component 102 that can generate a question based on a portion of current medical data received via the interface 108. Specifically, the patient 106 can converse with the medical professional 104 during an appointment, wherein such medical professional 104 can offer medical data (e.g., current medical data such as a diagnosis, a prognosis, an explanation, an answer, a statement, a response, etc.). The counselor component 102 can generate a question based on the current medical data received at the appointment. For example, the counselor component 102 can receive a current diagnosis (e.g., current medical data) for the patient 106 from the medical professional 104 in which the data store 204 having general medical knowledge can be leveraged in order to generate a question directed to the medical professional 104.

Furthermore, the counselor component 102 can include an aggregator component 402 that can accumulate the current medical data from the medical professional 104 in a standardized, uniform format. Since the current medical data is collected directly from the medical professional 104, the data can be considered "clean" and can be organized into a standardized format by the aggregator component 402. By aggregating the medical data in a standardized manner, a unified data storage facility/component can be employed to host medical data gathered during an appointment with the medical professional 104.

FIG. 4 additionally illustrates a system 404 that utilizes the "clean" source of information in the standardized format as a source to generate a question directed toward the medical professional 104. In other words, the system 404 can include the counselor component 102 that can utilize the aggregated data (e.g., the medical data collected from the medical professional 104 in a standardized uniform format) to generate a question to elicit an answer or response from the medical professional 104. Thus, a single schema can be employed with the current medical data. It is to be appreciated that the answer or response can further be collected and organized in a standardized format by the aggregator component 402 in order to capture "clean" data in a uniform manner. Thus, the system 400 can establish a "clean" set of data in a uniform manner that is representative of any medical data from an appointment with a plurality of medical professionals. The data store 204 can be personalized to describe and/or be associated with a given user/patient. In an additional aspect of the innovation, the personalized data store 204 and information can be aggregated, anonymized for privacy, to provide a source of data to improve accuracy of personalized counselor component 102.

Figure 5:
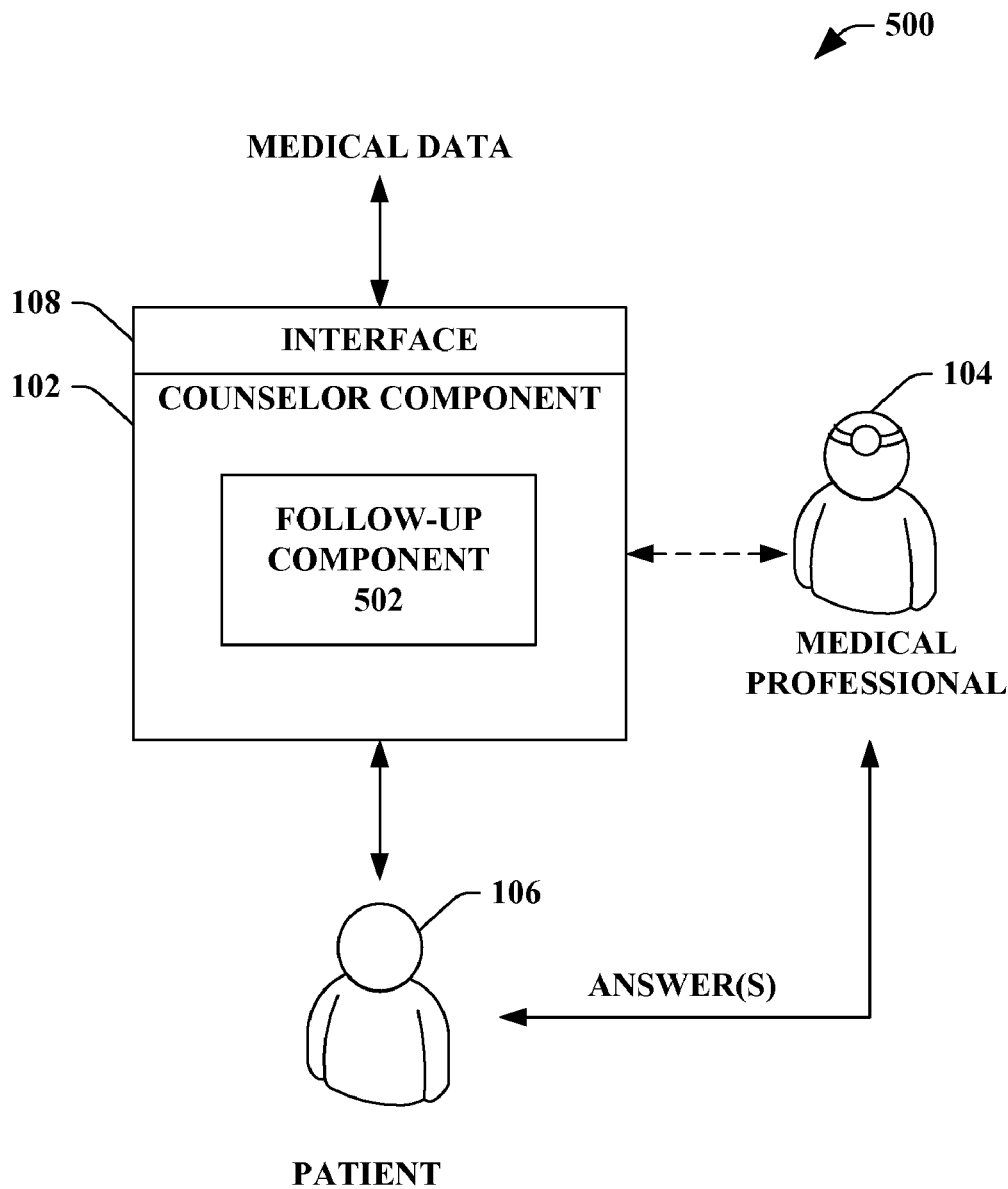
FIG. 5 illustrates a block diagram of an exemplary system that facilitates generating a follow-up question based upon an answer received from a medical professional.

FIG. 5 illustrates a system 500 that facilities generating a follow-up question based upon an answer received from a medical professional. The system 500 can include the counselor component 102 that can automatically provide a question to the patient 106 to ask the medical professional 104. For example, the patient 106 can be prompted to ask a question to the medical professional 104 based on received/gathered medical data. By giving the patient 106 a question to ask the medical professional 104, the appointment is greatly optimized to allow the medical professional 104 to answer/respond to all questions asked and the patient 106 gets an opportunity to ask all his or her questions.

The system 500 can further utilize a follow-up component 502 that can generate an additional question based at least in part upon an answer or response from the medical professional 104. For example, the counselor component 102 can generate a first question to elicit a response from the medical professional 104. Based on the received response (e.g., directly received, indirectly received, etc.) from the medical professional 104, the follow-up component 502 can evaluate such response and ascertain a follow-up question (e.g., a second question) accordingly. In particular, the follow-up component 502 can employ value of information (VOI) computations in order to ascertain an appropriate/ideal second question. For instance, VOI computations can be employed to identify a relevant question in light of the answer received by the medical professional 104 in response to the first question asked.

Figure 6:
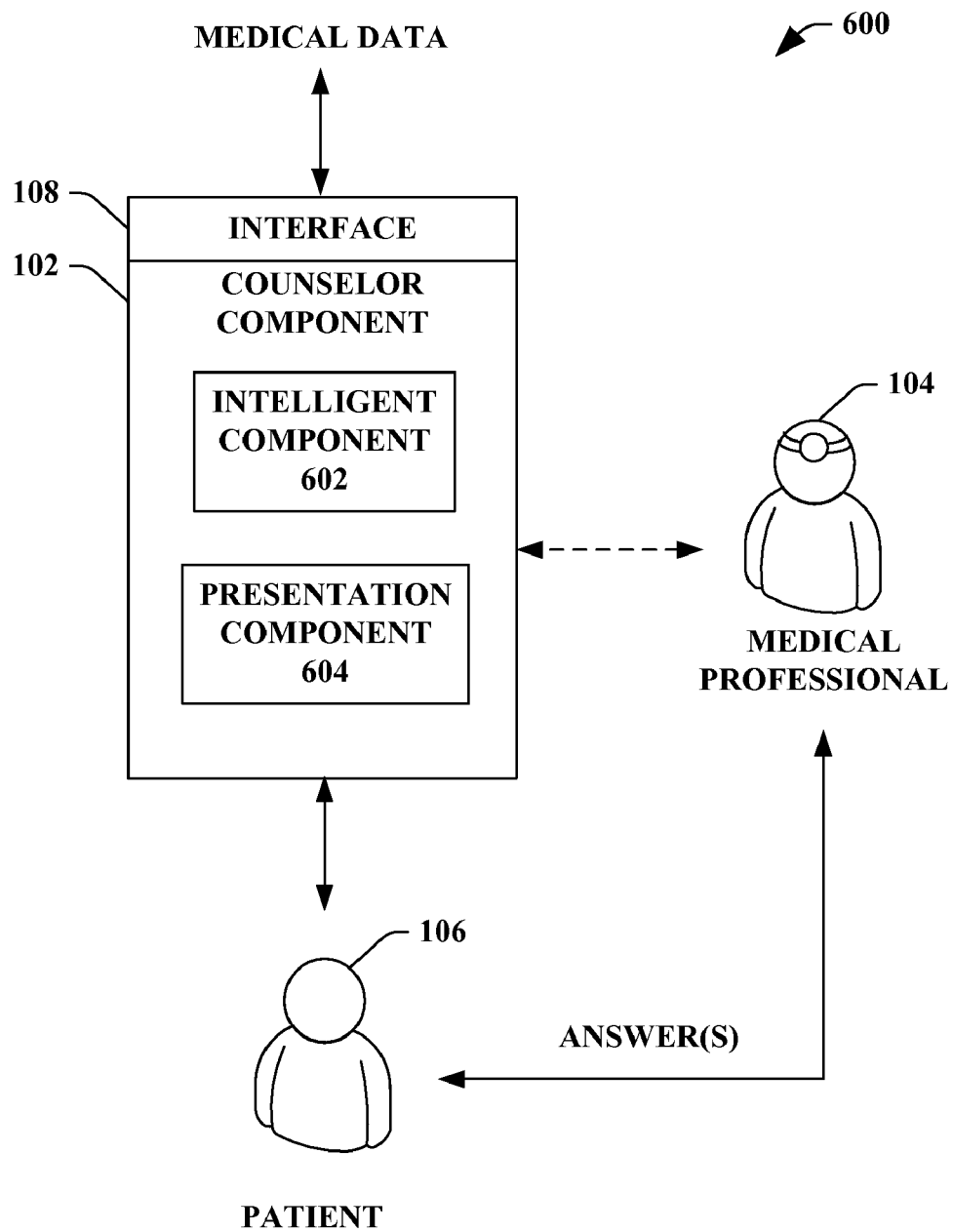
FIG. 6 illustrates a block diagram of an exemplary system that facilitates generating a question to ask a medical professional during a medical examination.

FIG. 6 illustrates a system 600 that employs intelligence to facilitate generating a question to ask a medical professional during a medical examination. The system 600 can include the counselor component 102, the medical professional 104, the patient 106, medical data, and the interface 108. It is to be appreciated that the counselor component 102, the medical professional 104, the patient 106, medical data, and the interface 108 can be substantially similar to respective components, professionals, patients, data, and interfaces described in previous figures. The system 600 further includes an intelligent component 602. The intelligent component 602 can be utilized by the counselor component 102 to facilitate automatically supplying a question that can be posed to the medical professional 104. For example, the intelligent component 602 can infer a question, a follow-up question, a potential question, a portion of medical data, a portion of general medical knowledge to utilize to generate a question, etc.

The intelligent component 602 can employ value of information (VOI) computation in order to identify questions to ask the medical professional. For instance, by utilizing VOI computation, the most ideal and/or appropriate questions can be determined. Moreover, it is to be understood that the intelligent component 602 can provide for reasoning about or infer states of the system, environment, and/or user from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources. Various classification (explicitly and/or implicitly trained) schemes and/or systems (e.g., support vector machines, neural networks, expert systems, Bayesian belief networks, fuzzy logic, data fusion engines . . . ) can be employed in connection with performing automatic and/or inferred action in connection with the claimed subject matter.

A classifier is a function that maps an input attribute vector, $x=(x1, x2, x3, x4, xn)$, to a confidence that the input belongs to a class, that is, $f(x)=confidence(class)$. Such classification can employ a probabilistic and/or statistical-based analysis (e.g., factoring into the analysis utilities and costs) to prognose or infer an action that a user desires to be automatically performed. A support vector machine (SVM) is an example of a classifier that can be employed. The SVM operates by finding a hypersurface in the space of possible inputs, which hypersurface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

The counselor component 102 can further utilize a presentation component 604 that provides various types of user interfaces to facilitate interaction between a user and any component coupled to the counselor component 102. As depicted, the presentation component 604 can be incorporated into the counselor component 102. However, it is to be appreciated that the presentation component 604 and/or similar view components can be a stand-alone unit and/or incorporated into the counselor component 102. The presentation component 604 can provide one or more graphical user interfaces (GUIs), command line interfaces, and the like. For example, a GUI can be rendered that provides a user with a region or means to load, import, read, etc., data, and can include a region to present the results of such. These regions can comprise known text and/or graphic regions comprising dialogue boxes, static controls, drop-down-menus, list boxes, pop-up menus, as edit controls, combo boxes, radio buttons, check boxes, push buttons, and graphic boxes. In addition, utilities to facilitate the presentation such as vertical and/or horizontal scroll bars for navigation and toolbar buttons to determine whether a region will be viewable can be employed. For example, the user can interact with one or more of the components coupled and/or incorporated into the counselor component 102. Specifically, the subject innovation can be utilized with a variety of hardware configurations such as, but not limited to disability assisted input/output facilities, voice enabled input/output, dactyl (e.g., Braille, etc.) keyboard, etc. Furthermore, the presentation component can be utilized in any suitable medical setting such as a disability assisted human computer interface.

The user can also interact with the regions to select and provide information via various devices such as a mouse, a roller ball, a keypad, a keyboard, a pen and/or voice activation, for example. Typically, a mechanism such as a push button or the enter key on the keyboard can be employed subsequent entering the information in order to initiate the search. However, it is to be appreciated that the claimed subject matter is not so limited. For example, merely highlighting a check box can initiate information conveyance. In another example, a command line interface can be employed. For example, the command line interface can prompt (e.g., via a text message on a display and an audio tone) the user for information via providing a text message. The user can then provide suitable information, such as alpha-numeric input corresponding to an option provided in the interface prompt or an answer to a question posed in the prompt. It is to be appreciated that the command line interface can be employed in connection with a GUI and/or API. In addition, the command line interface can be employed in connection with hardware (e.g., video cards) and/or displays (e.g., black and white, and EGA) with limited graphic support, and/or low bandwidth communication channels.

Figure 7:
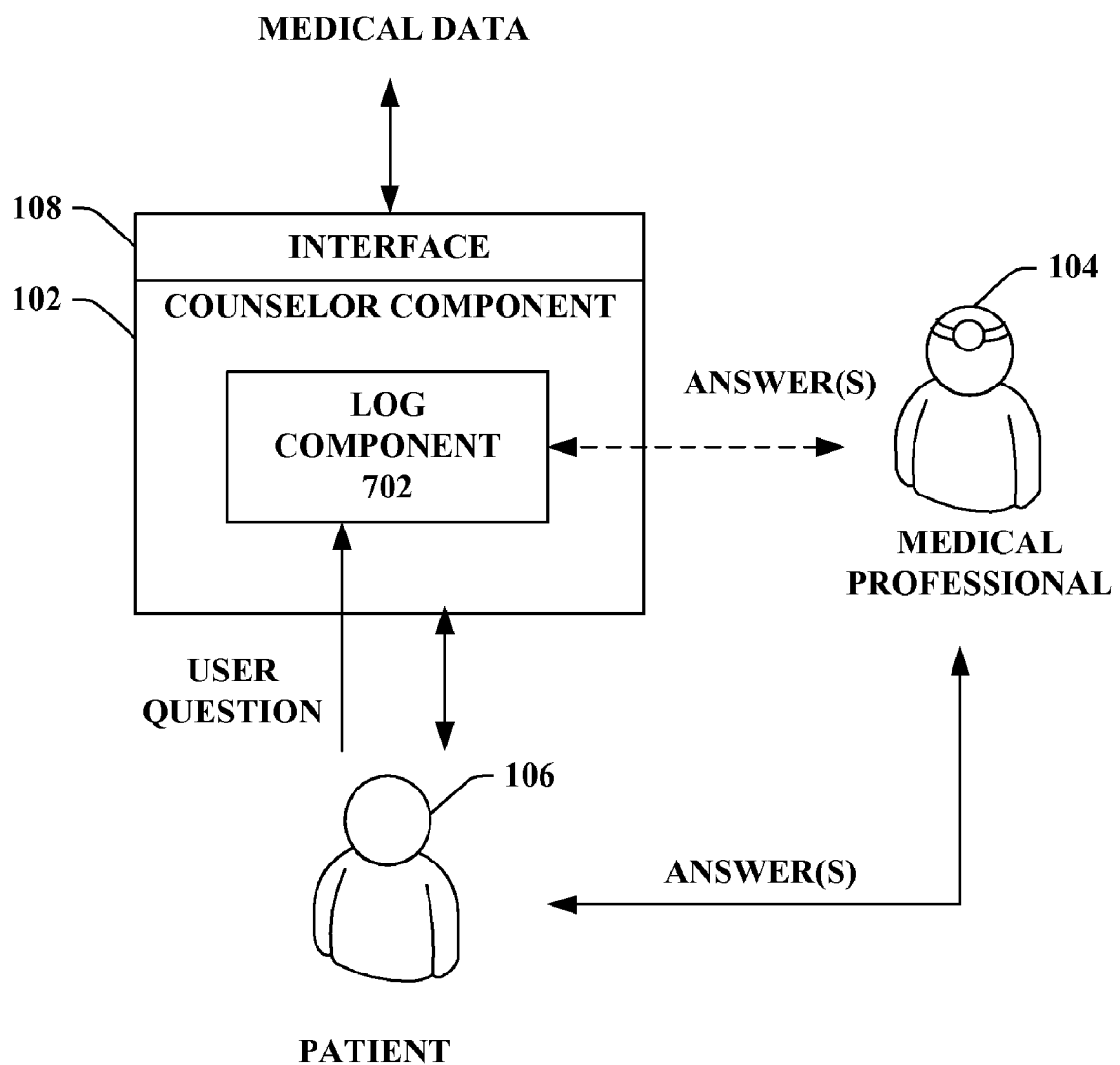
FIG. 7 a block diagram of exemplary system that facilitates gathering information that can be utilized during an appointment with a medical professional.

FIG. 7 illustrates a system 700 that facilitates gathering information that can be utilized during an appointment with a medical professional. The system 700 can employ the counselor component 102 that can gather medical information in order to generate a question to ask the medical professional 104. For instance, the patient 106 can be given a question to pose to the medical professional 104 in order to maximize the appointment therewith. The counselor component 102 can further implement a log component 702 that can collect at least one of a user-defined question, a response from the medical professional 104, or an answer from the medical professional 104.

In one example, the medical professional 104 can give a response or an answer that can be either directly captured by the log component 702 or received and inputted to the log component 702 by the patient 106. Thus, the log component 702 can be any suitable storage device, memory, recorder, and the like. In one particular aspect, the log component 702 can be a recording device that allows the patient 106 to review and recollect the answers, responses, etc. received from the medical professional 104 during an appointment. Therefore, the patient 106 can access the log component 702 after an appointment to refresh his or her memory in connection with the medical professional's advice (e.g., answers, responses, etc.). The log component 702 and a recording device can be also associated with automatic data recognition logic (e.g., speech recognition, etc.) to translate professional's responses into computer readable formats and augment data stores.

In another example, the log component 702 can gather a user-defined question for an appointment with the medical professional 104. For instance, the counselor component 102 can automatically generate questions to pose to the medical professional 104 but the patient 106 may still have their own questions they would like to ask. The log component 702 can record or receive such questions and provide the user-defined questions to the patient 106 to ask the medical professional 104 during the appointment accordingly. In addition, the user may be capable of immediate ranking of generated questions with subsequent updates of cloud based data store to assist machine learning algorithms.

In another aspect in accordance with the subject innovation, the counselor component 102 can generate a plurality of questions directed toward the medical professional 104, wherein the patient 106 can sort, filter, a re-phrase, and/or edit. For example, a question or a list of questions can be generated prior to or during an appointment with the medical professional 104 in which the patient 106 can re-arrange in order, edit, delete, rank in terms of importance, add, a re-phrase, etc. Therefore, the automatically generated list of questions can be specifically tailored to the particular patient 106. For example, a patient may delete a question based on pre-existing knowledge of such answer (e.g., the patient already knows the answer or response). User actions/modifications can be tracked and collected into a cloud store for subsequent data mining and system improvements.

Figure 8:
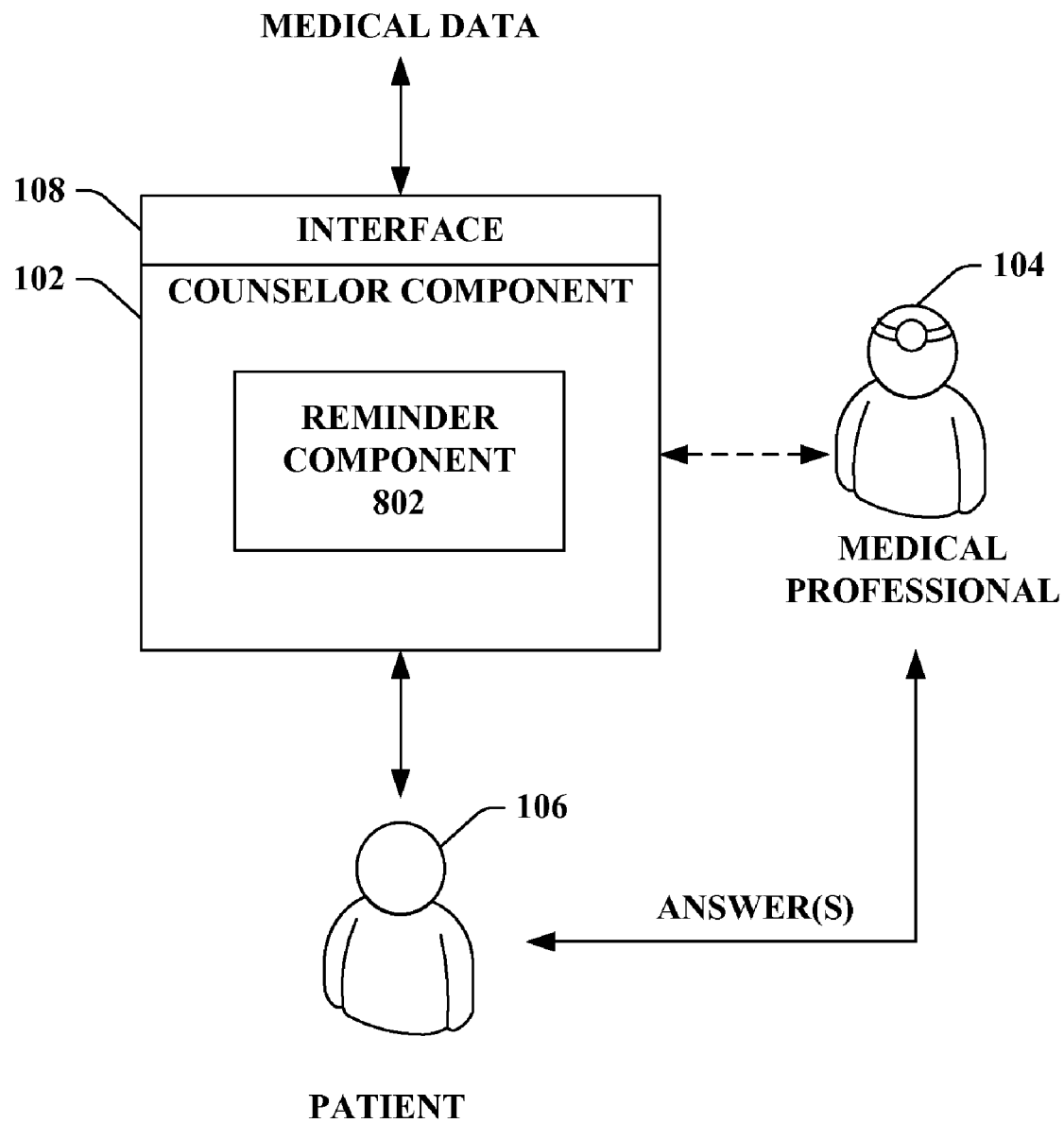
FIG. 8 illustrates a block diagram of an exemplary system that facilitates communicating a reminder in connection with an appointment with a medical professional.

FIG. 8 illustrates a system 800 that facilitates communicating a reminder in connection with an appointment with a medical professional. The system 800 can include the counselor component 102 that can identify and provide a question to the patient 106 to ask the medical professional 104. For instance, the medical professional 104 can utilize the questions and other medical data to proactively provide better patient care, wherein the medical professional 104 can evaluate and understand the typical questions that will be asked under certain circumstances. Moreover, the counselor component 102 can provide analysis of the patient data in a cloud (discussed in FIG. 3) prior to the arrival of the patient such that certain health conditions, prescriptions, appointments, lab results, etc. are considered to ensure questions are prominently displayed to the medical professional 104 to ask the patient when he or she arrives for the appointment.

The counselor component 102 can further employ a reminder component 802 that can provide a reminder to the patient 106 based on the answer, response, advice, diagnosis, treatment, etc. received during the appointment with the medical professional 104. Furthermore, the reminder component 802 can utilize the gathered medical data (e.g., answers, questions, medical history, diagnosis, prognosis, etc.) to remind the patient 106 of at least one of taking a medication, to go get lab work done, show up for a scheduled appointment, physical therapy appointment, pick up prescriptions, exercising, and/or any other suitable instruction that the medical professional 104 provided to the patient 106. It is to be appreciated that employing the reminder component 802 can translate into a large cost savings for the payor and/or the healthcare provider (e.g., the medical professional 104). Moreover, the reminder can be communicated to the patient 106 and/or medical professional 104 in any suitable manner such as, but not limited to, an email, a text message, a phone call, a cellular call, a mobile communication, a web alert, an instant message, web site posting, etc.

Figure 9:
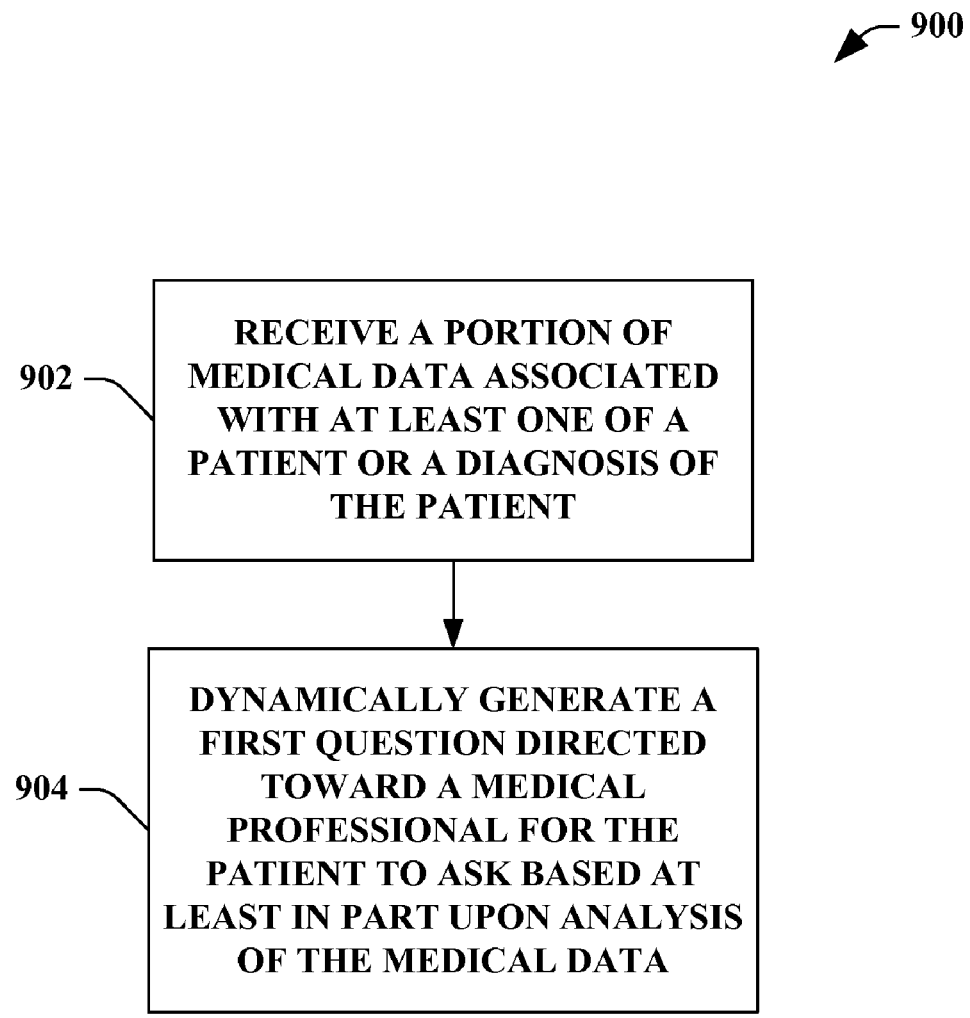
FIG. 9 illustrates an exemplary methodology for preparing a question for an appointment with a medical professional.
Figure 10:
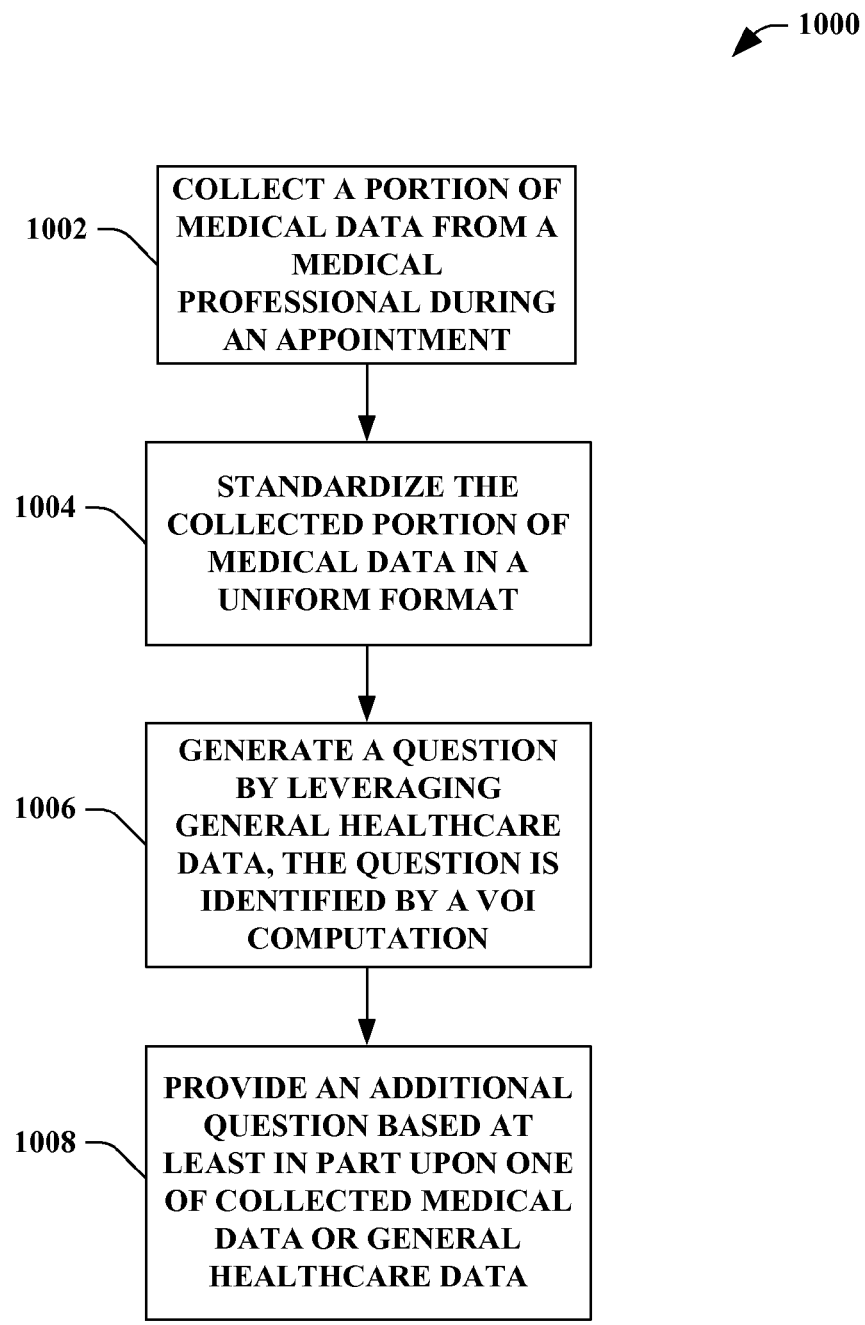
FIG. 10 illustrates an exemplary methodology that facilitates generating a question based upon an answer received from a medical professional.

FIGS. 9-10 illustrate methodologies and/or flow diagrams in accordance with the claimed subject matter. For simplicity of explanation, the methodologies are depicted and described as a series of acts. It is to be understood and appreciated that the subject innovation is not limited by the acts illustrated and/or by the order of acts. For example acts can occur in various orders and/or concurrently, and with other acts not presented and described herein. Furthermore, not all illustrated acts may be required to implement the methodologies in accordance with the claimed subject matter. In addition, those skilled in the art will understand and appreciate that the methodologies could alternatively be represented as a series of interrelated states via a state diagram or events. Additionally, it should be further appreciated that the methodologies disclosed hereinafter and throughout this specification are capable of being stored on an article of manufacture to facilitate transporting and transferring such methodologies to computers. The term article of manufacture, as used herein, is intended to encompass a computer program accessible from any computer-readable device, carrier, or media.

FIG. 9 illustrates a methodology 900 for preparing a question for an appointment with a medical professional. It is to be appreciated that the method 900 can employ identify based data/communication protection in order to ensure necessary confidentiality. At reference numeral 902, a portion of medical data associated with at least one of a patient or a diagnosis of the patient can be received. The medical data can be, but is not limited to being, a diagnosis, a prognosis, a medical record, a symptom, a medical evaluation, a prior medical condition, a medical condition, a disease, a virus, a blood type, an allergy, a test result, a blood pressure reading, a heart rate, an x-ray, an MRI, a scan, a CAT scan, a blood work result, a medical chart, a reading from a medical device, or a portion of information from a medical facility. For example, a portion of medical data can be received prior to an appointment, during an appointment, after an appointment, and/or any suitable combination thereof.

At reference numeral 904, a first question directed toward a medical professional for the patient to ask can be dynamically generated based at least in part upon analysis of the portion of medical data. It is to be appreciated that the medical professional can be any suitable medical related entity such as, but not limited to, a doctor, a nurse, a specialist, a surgeon, a medical student, a resident, a medical assistant, etc. For example, the first question can be generated based upon the received medical data in which the question can elicit an answer or a response from the medical professional in an efficient and time-consuming manner. By automatically supplying a question to a patient to pose to the medical professional, the patient can be sure to ask relevant and all questions he or she may have and the medical professional can be confident all questions are asked and answered.

FIG. 10 illustrates a methodology 1000 that facilitates generating a question based upon an answer received from a medical professional. It is to be appreciated that the method 1000 can employ identify based data/communication protection in order to ensure necessary confidentiality. At reference numeral 1002, a portion of medical data can be collected from a medical professional during an appointment for a patient. At reference numeral 1004, the collected portion of medical data can be standardized in a uniform format. Since such collected data is from the medical professional, such data can be considered "clean" and can be organized in a standardized manner to allow such data to be utilized universally (e.g., regardless of application type, software format, device standards, etc.).

At reference numeral 1006, a question can be generated by leveraging general healthcare data, wherein the question can be identified by a value of information (VOI) computation. The general healthcare data can be utilized to identify an initial question to pose to the medical professional based on an initial diagnosis or response from the medical professional during the appointment. A question can be identified based in part upon implementing the VOI computation to select a high-valued questions based on VOI technical algorithms and/or techniques.

At reference numeral 1008, an additional question can be provided based at least in part upon one of collected medical or general healthcare data. Thus, the additional question can be generated based upon an answer from the initial question asked (e.g., such information is standardized and collected in a uniform format) and/or general healthcare data (e.g., a medical data base, a medical data storage facility, a web site, a web forum, etc.).

Figure 11:
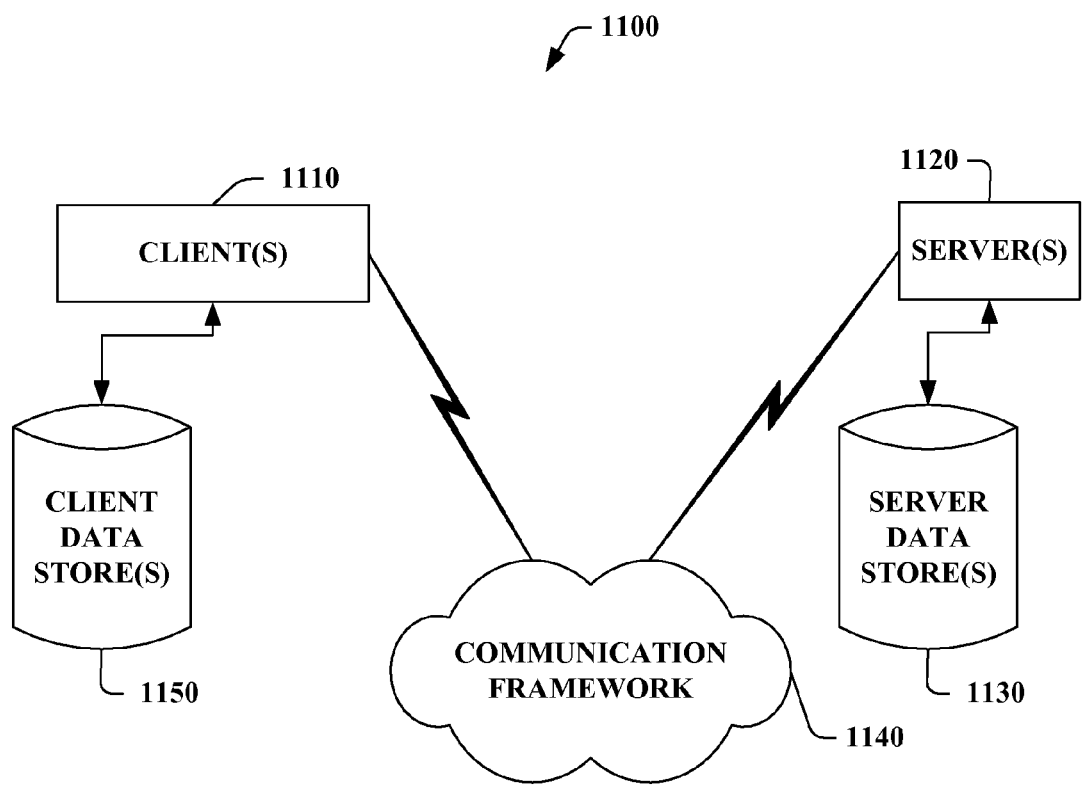
FIG. 11 illustrates an exemplary networking environment, wherein the novel aspects of the claimed subject matter can be employed.
Figure 12:
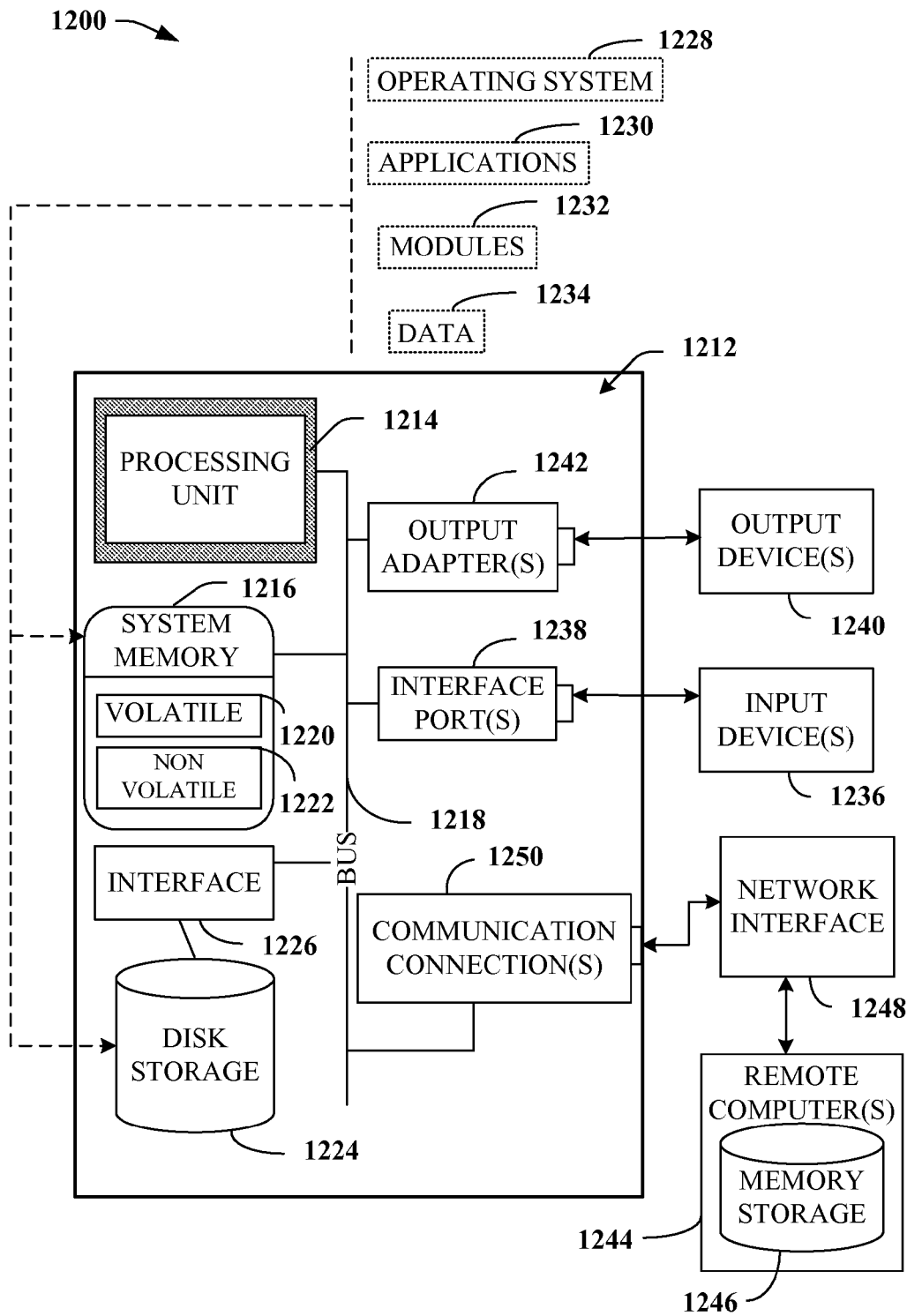
FIG. 12 illustrates an exemplary operating environment that can be employed in accordance with the claimed subject matter.

In order to provide additional context for implementing various aspects of the claimed subject matter, FIGS. 11-12 and the following discussion is intended to provide a brief, general description of a suitable computing environment in which the various aspects of the subject innovation may be implemented. For example, a counselor component that facilitates automatically generating questions to ask a doctor during an appointment, as described in the previous figures, can be implemented in such suitable computing environment. While the claimed subject matter has been described above in the general context of computer-executable instructions of a computer program that runs on a local computer and/or remote computer, those skilled in the art will recognize that the subject innovation also may be implemented in combination with other program modules. Generally, program modules include routines, programs, components, data structures, etc., that perform particular tasks and/or implement particular abstract data types.

Moreover, those skilled in the art will appreciate that the inventive methods may be practiced with other computer system configurations, including single-processor or multi-processor computer systems, minicomputers, mainframe computers, as well as personal computers, hand-held computing devices, microprocessor-based and/or programmable consumer electronics, and the like, each of which may operatively communicate with one or more associated devices. The illustrated aspects of the claimed subject matter may also be practiced in distributed computing environments where certain tasks are performed by remote processing devices that are linked through a communications network. However, some, if not all, aspects of the subject innovation may be practiced on stand-alone computers. In a distributed computing environment, program modules may be located in local and/or remote memory storage devices.

FIG. 11 is a schematic block diagram of a sample-computing environment 1100 with which the claimed subject matter can interact. The system 1100 includes one or more client(s) 1110. The client(s) 1110 can be hardware and/or software (e.g., threads, processes, computing devices). The system 1100 also includes one or more server(s) 1120. The server(s) 1120 can be hardware and/or software (e.g., threads, processes, computing devices). The servers 1120 can house threads to perform transformations by employing the subject innovation, for example.

One possible communication between a client 1110 and a server 1120 can be in the form of a data packet adapted to be transmitted between two or more computer processes. The system 1100 includes a communication framework 1140 that can be employed to facilitate communications between the client(s) 1110 and the server(s) 1120. The client(s) 1110 are operably connected to one or more client data store(s) 1150 that can be employed to store information local to the client(s) 1110. Similarly, the server(s) 1120 are operably connected to one or more server data store(s) 1130 that can be employed to store information local to the servers 1120.

With reference to FIG. 12, an exemplary environment 1200 for implementing various aspects of the claimed subject matter includes a computer 1212. The computer 1212 includes a processing unit 1214, a system memory 1216, and a system bus 1218. The system bus 1218 couples system components including, but not limited to, the system memory 1216 to the processing unit 1214. The processing unit 1214 can be any of various available processors. Dual microprocessors and other multiprocessor architectures also can be employed as the processing unit 1214.

The system bus 1218 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI).

The system memory 1216 includes volatile memory 1220 and nonvolatile memory 1222. The basic input/output system (BIOS), containing the basic routines to transfer information between elements within the computer 1212, such as during start-up, is stored in nonvolatile memory 1222. By way of illustration, and not limitation, nonvolatile memory 1222 can include read only memory (ROM), programmable ROM (PROM), electrically programmable ROM (EPROM), electrically erasable programmable ROM (EEPROM), or flash memory. Volatile memory 1220 includes random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), Rambus direct RAM (RDRAM), direct Rambus dynamic RAM (DRDRAM), and Rambus dynamic RAM (RDRAM).

Computer 1212 also includes removable/non-removable, volatile/nonvolatile computer storage media. FIG. 12 illustrates, for example a disk storage 1224. Disk storage 1224 includes, but is not limited to, devices like a magnetic disk drive, floppy disk drive, tape drive, Jaz drive, Zip drive, LS-100 drive, flash memory card, or memory stick. In addition, disk storage 1224 can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 1224 to the system bus 1218, a removable or non-removable interface is typically used such as interface 1226.

It is to be appreciated that FIG. 12 describes software that acts as an intermediary between users and the basic computer resources described in the suitable operating environment 1200. Such software includes an operating system 1228. Operating system 1228, which can be stored on disk storage 1224, acts to control and allocate resources of the computer system 1212. System applications 1230 take advantage of the management of resources by operating system 1228 through program modules 1232 and program data 1234 stored either in system memory 1216 or on disk storage 1224. It is to be appreciated that the claimed subject matter can be implemented with various operating systems or combinations of operating systems.

A user enters commands or information into the computer 1212 through input device(s) 1236. Input devices 1236 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1214 through the system bus 1218 via interface port(s) 1238. Interface port(s) 1238 include, for example, a serial port, a parallel port, a game port, and a universal serial bus (USB). Output device(s) 1240 use some of the same type of ports as input device(s) 1236. Thus, for example, a USB port may be used to provide input to computer 1212, and to output information from computer 1212 to an output device 1240. Output adapter 1242 is provided to illustrate that there are some output devices 1240 like monitors, speakers, and printers, among other output devices 1240, which require special adapters. The output adapters 1242 include, by way of illustration and not limitation, video and sound cards that provide a means of connection between the output device 1240 and the system bus 1218. It should be noted that other devices and/or systems of devices provide both input and output capabilities such as remote computer(s) 1244.

Computer 1212 can operate in a networked environment using logical connections to one or more remote computers, such as remote computer(s) 1244. The remote computer(s) 1244 can be a personal computer, a server, a router, a network PC, a workstation, a microprocessor based appliance, a peer device or other common network node and the like, and typically includes many or all of the elements described relative to computer 1212. For purposes of brevity, only a memory storage device 1246 is illustrated with remote computer(s) 1244. Remote computer(s) 1244 is logically connected to computer 1212 through a network interface 1248 and then physically connected via communication connection 1250. Network interface 1248 encompasses wire and/or wireless communication networks such as local-area networks (LAN) and wide-area networks (WAN). LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1250 refers to the hardware/software employed to connect the network interface 1248 to the bus 1218. While communication connection 1250 is shown for illustrative clarity inside computer 1212, it can also be external to computer 1212. The hardware/software necessary for connection to the network interface 1248 includes, for exemplary purposes only, internal and external technologies such as, modems including regular telephone grade modems, cable modems and DSL modems, ISDN adapters, and Ethernet cards.

What has been described above includes examples of the subject innovation. It is, of course, not possible to describe every conceivable combination of components or methodologies for purposes of describing the claimed subject matter, but one of ordinary skill in the art may recognize that many further combinations and permutations of the subject innovation are possible. Accordingly, the claimed subject matter is intended to embrace all such alterations, modifications, and variations that fall within the spirit and scope of the appended claims.

In particular and in regard to the various functions performed by the above described components, devices, circuits, systems and the like, the terms (including a reference to a "means") used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter. In this regard, it will also be recognized that the innovation includes a system as well as a computer-readable medium having computer-executable instructions for performing the acts and/or events of the various methods of the claimed subject matter.

There are multiple ways of implementing the present innovation, e.g., an appropriate API, tool kit, driver code, operating system, control, standalone or downloadable software object, etc. which enables applications and services to use the advertising techniques of the invention. The claimed subject matter contemplates the use from the standpoint of an API (or other software object), as well as from a software or hardware object that operates according to the advertising techniques in accordance with the invention. Thus, various implementations of the innovation described herein may have aspects that are wholly in hardware, partly in hardware and partly in software, as well as in software.

The aforementioned systems have been described with respect to interaction between several components. It can be appreciated that such systems and components can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components, and any one or more middle layers, such as a management layer, may be provided to communicatively couple to such sub-components in order to provide integrated functionality. Any components described herein may also interact with one or more other components not specifically described herein but generally known by those of skill in the art.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

What is claimed is:

1. A computer implemented system that facilitates and effectuates dynamically providing questions for a patient to ask a medical professional during an appointment, comprising:
   one or more processors;
   an interface that receives a portion of medical data;
   a counselor component, executable by the one or more processors, that:
      generates a first question based on the portion of medical data and communicates the first question to the patient via the interface, wherein the first question is generated to elicit an answer from the medical professional during the appointment;
      receives the answer; and
      dynamically generates a second question directed toward the medical professional based on the answer; and
   a reminder component, executable by the one or more processors, that sets a reminder based on the answer from the medical professional and communicates the reminder to the patient at a time after the appointment.

2. The system of claim 1, wherein the portion of medical data is at least one of a diagnosis, a prognosis, a medical record, a symptom, a medical evaluation, a prior medical condition, a medical condition, a disease, a virus, a blood type, an allergy, a test result, a blood pressure reading, a heart rate, an x-ray, an MRI, a scan, a CAT scan, a blood work result, a medical chart, a reading from a medical device, or a portion of information from a medical facility.

3. The system of claim 1, wherein at least one of the counselor component or the interface are incorporated into a portable device that can communicate the first question to the patient, the portable device being at least one of a smartphone, a cell phone, a mobile communication device, a portable digital assistant (PDA), a laptop, a pocket PC, a desktop, a gaming device, a portable media player, a media device, a tablet PC, a handheld, a wireless browsing device, an electronic organizer, a gaming console, or a device with Internet connectivity.

4. The system of claim 1, wherein the counselor component is incorporated into a cloud, the cloud being at least one resource that is maintained by a party and accessible by the patient over a network.

5. The system of claim 4, further comprising a device that receives the first question over the network.

6. The system of claim 1, further comprising an aggregator component that collects at least one of the answer from the medical professional or a statement from the medical professional in a standardized, uniform format.

7. The system of claim 6, wherein the aggregator component establishes a data base including the standardized uniformly formatted data related to the at least one of the answer or the statement, the data base being leveraged by the counselor component for automatic question generation.

8. The system of claim 1, further comprising a log component that records at least one of the answer from the medical professional, a statement from the medical professional, a response from the medical professional, the first or second question posed to the medical professional, or a patient-defined question.

9. The system of claim 1, wherein the counselor component is a self improving computing cloud that tracks and collects modifications to questions.

10. The system of claim 9, wherein the counselor component enables the patient to edit the questions, wherein the edit is at least one of a deletion, a sorting of the questions, a re-arrangement order of the questions, a ranking of importance for the questions, or a re-phrasing of the questions.

11. The system of claim 10, wherein the modifications are stored in the computing cloud for subsequent data mining and further improvements for question generation.

12. The system of claim 1, wherein the reminder relates to at least one of taking a medication, getting lab work done, an upcoming appointment, picking up a prescription, exercising, or following an instruction received from the medical professional during the appointment.

13. The system of claim 1, wherein the reminder is communicated to the patient with at least one of an email, a text message, a phone call, a cellular call, a mobile communication, a web alert, an instant message, or a web site posting.

14. The system of claim 1, wherein the counselor component receives the answer directly from the medical professional and utilizes a speech recognition process to comprehend the answer.

15. The system of claim 1, wherein the counselor component receives the answer indirectly from the medical professional via the patient.

16. A computer-implemented method that employs one or more processors to facilitate generating a question for an appointment with a medical professional, comprising:
   receiving a portion of medical data associated with at least one of a patient or a diagnosis of the patient;
   dynamically generating, via the one or more processors, a first question directed toward the medical professional for the patient to ask based at least on an analysis of the portion of medical data;
   receiving an answer in response to the first question from the medical professional;
   producing, via the one or more processors, a second question for the medical professional based on the answer;

setting, via the one or more processors, a reminder based on the answer; and communicating the reminder to the patient at a time after the appointment is completed.

17. The method of claim 16, further comprising utilizing a value of information (VOI) computation to generate at least one of the first question or the second question.

18. The method of claim 16, further comprising:

collecting at least one of a statement from the medical professional or the answer from the medical professional; and standardizing the collection into a uniform format.

19. A computer implemented system comprising:

one or more processors;

an interface that receives medical data for a patient; and a counselor component, executable by the one or more processors, that:

generates a plurality of questions based on the medical data and communicates the plurality of questions to the patient, wherein the plurality of questions are generated for the patient to elicit answers from a medical professional during an appointment;

enables the patient to rank the plurality of questions according to importance;

tracks the ranking of the plurality of questions and collects data associated with the ranking to store in a cloud computing environment for data mining and system improvements;

receives a first answer from the medical professional responsive to a first question asked by the patient; and employs a value of information (VOI) computation to generate a second question based on the first answer.

20. The system of claim 19, further comprising a reminder component, executable by the one or more processors, that sets a reminder for the patient based on the first answer, and communicates the reminder to the patient at a later time after the appointment is completed, wherein the reminder relates to at least one of taking a medication, another upcoming appointment, picking up a prescription, exercising, or following an instruction received from the medical professional during the appointment.

* * * * *

UNITED STATES PATENT AND TRADEMARK OFFICE
CERTIFICATE OF CORRECTION

| | | |
|---|---|---|
| PATENT NO. | : 7,908,151 B2 | Page 1 of 1 |
| APPLICATION NO. | : 11/864599 | |
| DATED | : March 15, 2011 | |
| INVENTOR(S) | : David E. Heckerman et al. | |

It is certified that error appears in the above-identified patent and that said Letters Patent is hereby corrected as shown below:

Title Page, Item (75), under "Inventors" column 1, lines 9-10, delete "Hurbert Van Hoof," and insert -- Hubert Van Hoof, --, therefor.

Signed and Sealed this
Twenty-sixth Day of July, 2011

David J. Kappos
*Director of the United States Patent and Trademark Office*